United States Patent [19]
Daynes et al.

[11] Patent Number: 5,827,841
[45] Date of Patent: Oct. 27, 1998

[54] METHOD FOR ENHANCEMENT OF PRODUCTION OF LYMPHOKINES AND APPLICATIONS THEREOF

[75] Inventors: Raymond A. Daynes; Barbara A. Araneo, both of Salt Lake City, Utah

[73] Assignee: University of Utah Research Foundation, Salt Lake City, Utah

[21] Appl. No.: 295,068

[22] Filed: Sep. 20, 1994

Related U.S. Application Data

[62] Division of Ser. No. 018,471, Feb. 16, 1993, Pat. No. 5,540,919, which is a continuation of Ser. No. 412,270, Sep. 25, 1989, abandoned.

[51] Int. Cl.⁶ ............................ A01N 45/00; A61K 31/56
[52] U.S. Cl. ................... 514/169; 435/70.1; 435/135; 514/170; 514/171; 514/178
[58] Field of Search ................... 435/70.1, 135; 514/169, 170, 171, 178

[56] References Cited

U.S. PATENT DOCUMENTS

| | | | |
|---|---|---|---|
| 4,496,556 | 1/1985 | Orentreich | 514/178 |
| 4,518,595 | 5/1985 | Coleman et al. | 514/178 |
| 4,542,129 | 9/1985 | Orentreich | 514/178 |
| 4,628,052 | 12/1986 | Peat | 514/171 |
| 4,778,750 | 10/1988 | Gottlieb | 435/5 |
| 4,789,658 | 12/1988 | Yoshimoto et al. | 514/12 |
| 5,407,684 | 4/1995 | Loria et al. | |

FOREIGN PATENT DOCUMENTS

| | | |
|---|---|---|
| 608824 | 12/1990 | Australia . |
| 0 133 995 | 8/1984 | European Pat. Off. . |
| 0 282 156 | 1/1988 | European Pat. Off. . |
| 2204237 | 4/1988 | United Kingdom . |

OTHER PUBLICATIONS

Risdon, G. et al. (1990). Mechanisms of Chemoprevention by Dietary Dehydroisoandrosterone: Inhibition of Lymphopoiesis,: *Am. J. Pathol.* 136(4):759–69, [Abstract].

Matsunaga, A. et al. (1989). "Dehydroisoandrosterone Prevention of Autoimmune Disease in NZB/W F1 Mice: Lack of an Effect on Associated Immunological Abnomalities, " *Biochim.Biophys.*ACTA 992(3):265–71, [Abstract].

Windruch, R. et al. (1984). "Food Intake Reduction and Immunologic Alterations in Mice Fed Dehydrorepiandrosterone," *Exp. Gerontol.* 19(5):297–304, [Abstract].

Dolecek, R. (1989). "Endocrine Changes After Burn Trauma–A Review", *Keio J. Med.* 38(3):262–276.

Coffman, R. (1989). "T–Helper Heterogeneity and Immune Response Patterns", *Hosp. Practice*, 15 Aug. 1989, pp. 101–133.

Bhalla, A.K. (1989). "Review: Hormones and the Immune Response,"*Ann. Rheum. Dis.*48:1–6.

Daynes, R.A. et al. (1989). "Contrasting effects of Glucocorticoids on the Capacity of T Cells to Produce the Growth Factors Interleukin 2 and Interleukin 4", *Eur. J. Immunol.* 19(12), pp. 2319–2825.

Orentreich, N. et al. (1984). "Age Changes and Sex Differences in Serum Dehydroepiandrosterone Sulfate Concentrations Throughout Adulthood,"*J. Clin. Endocrin. Metab.*59:3, pp. 551–555.

Weindruch, R. et al. (1984). "Foord Intake Reduction and Immunologic Alterations in Mice Fed Dehydroepiandrosterone", *Exper. Gerontol.*19:297–304.

Loria, R. et al. (1988). "Protection Against Acute Lethal Viral Infections With the Native Steroid Dehydroepiandrosterone (DHEA)", *J. Med. Virol.* 26:301–314.

Gordon, G. et al. (1987). "Modulation of Growth, Differentiation and Carcinogenesis by Dehydroepiandrosterone", *Adv. Enz. Regul.* 26:355–378.

Regelson, W. et al. (1988). "Hormonal Intervention: Buffer Hormones or State Dependency: The Role of Dehydroepiandrosterone (DHEA), Thyroid Hormone, Estrogen and Hypophysectomy in Aging, "*Ann. N.Y. Acad. Sci.*518:260–273.

*Primary Examiner*—Leon B. Lankford, Jr.
*Attorney, Agent, or Firm*—Venable, Baetjer, Howard & Civiletti, LLP

[57] ABSTRACT

Disclosed is a method for enhancing the production of T cell lymphokines, which comprises exposing T cell lymphocytes which have a potential to make selected T cell lymphokines to an appropriate concentration of at least one particular steroid hormone prior to cellular activation. Also disclosed are applications of the method for clinically diagnosing abnormal interleukin production, maintaining in vitro tissue cultures of T cells, overcoming certain types of immunosuppression caused by elevated GCS levels, caused by endogenous production or exogenous administration, use as a vaccine adjuvant to selectively direct the vaccine-induced immune response down a protective, rather than a potentially pathologic or non-protective, immunologic pathway, as a treatment for naturally occuring aging-related decreases in immune function, as a treatment for stress or trauma-induced decreases in immune function, and as a means to facilitate desensitization to agents to which a warm-blooded animal is allergic.

6 Claims, 7 Drawing Sheets

METHOD FOR ENHANCEMENT OF PRODUCTION OF LYMPHOKINES AND APPLICATIONS THEREOF

This application is a divisional of application Ser. No. 08/018,471, filed Feb. 16, 1993, now U.S. Pat. No. 5,540,919 which is a continuation of application Ser. No. 07/412,270, filed Sep. 25, 1989 now abandoned.

BACKGROUND OF THE INVENTION

1. Field

The invention relates to regulation of cytokine production, particularly in vitro and in vivo enhancement of lymphokine production by T cell lymphocytes which are exposed to particular types of steroid hormones prior to cellular activation, and applications thereof.

2. State of the Art

It is known that lymphocytes exported from the thymus undergo a series of differentiation events which confer upon them the capacity to recognize and respond to specific peptide antigens presented appropriately in the context of self major histocompatibility complex (MHC) molecules (Bevan, J. Exp. Med., 142:1349 (1975); Zinkernagel et al., J. Exp. Med., 141:1427 (1975)). Mechanistically, thymic maturation is a complex process which includes an irreversible rearrangement of T cell receptor genes (Hedrick et al. Nature, 308:149 (1984); Yanagi et al., Nature, 308:145 (1984)), the cell surface expression of these gene products as a disulfide-linked heterodimer (Meur et al., J. Exp. Med., 158:988 (1983); Kappler et al., Cell, 35:295 (1983)), positive and negative selection processes to provide appropriate restriction and avoidance of self reactivity (Von Boehmer et al., Immunol. Rev., 101:5 (1988)), and the synthesis and expression of CD4 or CD8 as accessory adhesion molecules (Bierer et al., Ann. Rev. Immunol., 7:579 (1989); Dembic et al., Nature, 320:232 (1986)). Microenvironmental influences within the thymus play an essential role in the fidelity of this process.

Subsequent to leaving the thymic microenvironment, mature T lymphocytes gain access to the recirculating T cell pool where they move freely via the blood between mucosal and nonmucosal lymphoid compartments in the mammalian host (Hamann et al., Immunol. Rev., 108:19 (1989)). T-lymphocyte expression of lymphoid tissue-specific homing receptors, which are complementary for vascular addressins on high endothelial venules present in Peyer's patches and peripheral lymph nodes, provide a biochemical means for selectivity to this recirculation process (Hamann et al., Immunol. Rev., 108:19 (1989)). Non-activated lymphocytes can move freely between mucosal and nonmucosal lymphoid tissues due to the presence of both types of homing receptors on their plasma membranes (Pals et al. Immunol., Rev., 108:111 (1989)). Effector lymphocytes, and antigen-activated immunoblasts which are stimulated in a particular site in the body, however, exhibit a far more selective migratory behavior. These cells move primarily to tissues originally involved in antigen exposure and cellular activation (Hamann et al., Immunol. Rev., 108:19 (1989); Pals et al., Immunol. Rev., 108:111 (1989)).

An immune response is initiated following T cell recognition of antigen peptides in the context of self MHC molecules and generally takes place in one of the host's secondary lymphoid compartments. Cellular activation is triggered by the binding of antigen to the T cell receptor (TCR), forming an antigen/TCR complex which transducers the antigen-specific extracellular stimulation across the plasma membrane, and generates intracellular signals which include the activation of protein kinase C and the increases in intracellular calcium (Alcover et al., Immunol. Rev., 95:5 (1987); Gelfand et al., Immunol. Rev., 95:59 (1987)). While signal transduction can lead to T cell unresponsiveness (Mueller et al., Ann. Rev. Immunol., 7:445 (1989)), positive signal transduction events trigger a series of additional biochemical processes. One consequence of this activation is the stimulated production of a number of biologically active molecules which are collectively termed lymphokines (Alcover et al., Immunol. Rev., 95:5 (1987); Gelfand et al., Immunol. Rev., 95:59 (1987)).

The lymphokines, many of which function primarily through autocrine and paracrine mechanisms, serve to mediate numerous effector functions controlled by T cells through their capacity to regulate cellular proliferation, differentiation and maturation events in lymphocytes, plus other hematopoietic and somatic tissue cells (Paul, Cell, 57:521 (1989)).

Each of the various types of lymphokines exhibit pleiotropic activities, dependent upon the specific type of cellular targets being stimulated. The biological evaluation of recombinant forms of specific lymphokines has determined that individual species can possess both distinct and overlapping cellular activities (Paul, Cell, 57:521 (1989); Mossman et al., Ann. Rev. Immunol., 7:145 (1989)). Interleukin-2 (IL-2) and interleukin-4 (IL-4), for example, share the capacity to facilitate T cell growth but are disparate in their relative contribution to cellular and humoral immune responses. Cloned T cell lines, restricted in their capacity to produce individual species of lymphokines, have been described which demonstrate unique capabilities in serving as effector cells or helper cells for various types of immune responses (Paul, Cell, 57:521 (1989); Mossman et al., Ann. Rev. Immunol., 7:145 (1989); Hayakawa et al., J. Exp Med., 168:1825 (1988)).

Immunosuppression in animals can result from a depressed capacity to produce species of lymphokines which are essential to the development of protective forms of immunity. Imbalances between various types of lymphokines, where species of lymphokines capable of promoting one form of immune response exhibit enhanced production, while those lymphokines needed to promote protective forms of immunity are suppressed, can also lead to immunosuppression. It is known that animals may be immunosuppressed as a consequence of endogenous elevations in adrenal glucocorticosteroid (GCS) levels. This condition could result from viral infections, certain bacterial infections, certain parasitic infections, cancer, some autoimmune syndromes, stress, trauma, post-surgical trauma, burn trauma or as a secondary consequence to any clinical condition which causes an elevated production of interleukin-1 (IL-1). Plasma GCS levels can also be elevated exogenously as a consequence of therapeutic treatment for a variety of clinical conditions. It is also well known that certain essential functions of the immune system decline with age, a situation which correlates with elevations in adrenal output of GCS and depressions in production of other types of adrenal steroid hormones.

Known pharmaceutical products and theraputic methods for treating immunosuppressed animals having depressions or imbalances in their ability to produce interleukins have focused on the production and purification of IL-2 by activated T cells, or the production of IL-2 through genetic engineering techniques, followed by the therapeutic administration of this IL-2 or IL-2 administration with a muramyl-dipeptide in an attempt to restore normal propagation of T cells. Illustrative of such prior art are the disclosures of U.S. Pat. No. 4,661,447 issued Apr. 28, 1987 to Fabricius et al., U.S. Pat. No. 4,780,313 issued Oct. 25, 1988 to Koichiro et al. and U.S. Pat. No. 4,789,658 issued Dec. 6, 1988 to Yoshimoto et al. The side effects of therapeutic approaches of the prior art of systemic administration of recombinant IL-2 are numerous. Such side effects include fever, hypotension, hepatic and renal failure, myocardial infarctions, capillary leak syndrome, and massive edema (Dinatello et al., New England J. of Med., 317:940 (1987)).

Also disclosed in the prior art is the theraputic use of the adrenal androgen steroid dehydroepiandrosterone (DHEA) to treat maladies such as diabetes, dry skin, occular hypertension, obesity, and retroviral infections. Illustrative of such prior art teachings are the disclosures of U.S. Pat. No. 4,395,408 issued Jul. 26, 1983 to Torelli et al., U.S. Pat. No. 4,518,595 issued May 21, 1985 to Coleman et al., U.S. Pat. No. 4,542,129 issued Sep. 17, 1985 to Orentreich, U.S. Pat. No. 4,617,299 issued Oct. 14, 1986 to Knepper, U.S. Pat. No. 4,628,052 issued Dec. 9, 1986 to Peat, U.S. Pat. No. 4,666,898 issued May 19, 1987 to Coleman et al., European Patent Application No. 0 133 995 A2 dated Feb. 8, 1984 (inventor: Schwartz et al.), and UK Patent Application No. GB 2 204 237 A dated Apr. 14, 1988 (inventor: Prendergast).

SUMMARY OF THE INVENTION

Objectives: It is an objective of the invention to provide a method for enhancing the biosynthesis of selected lymphokines by activated T cells. Another objective of the invention is to enhance immune functions in warm blooded animals by restoring their capacity to naturally produce physiological concentrations of these lymphokines with a minimization of side effects. Further objectives of the invention are to provide applications of the method for clinically diagnosing deficiencies of interleukin production, maintaining in vitro tissue cultures of T cells, and overcoming certain types of immunosuppression caused by elevated GCS levels, caused by endogenous production or exogenous administration. Final objectives of the invention are to provide applications of the method as a vaccine adjuvant to selectively direct the vaccine-induced immune response down a protective, rather than a potentially pathologic or non-protective, immunologic pathway, as a treatment for naturally occuring aging-related decreases in immune function, as a treatment for stress or trauma-induced decreases in immune function, and as a means to facilitate desensitization to agents to which a warm-blooded animal is allergic.

Features: In the accomplishment of the foregoing objectives of the invention, T cell lymphocytes which have a potential to make selected T cell lymphokines are exposed to particular types of steroid hormones prior to activation. This exposure results in an enhanced cellular potential for production of certain T cell lymphokines, and, following cellular activation, if the concentration of the particular steroid hormone is appropriate, the biosynthesis and secretion of certain T cell lymphokines will be maximized.

In another aspect of the invention, a diagnostic test for evaluating lymphokine production deficiencies is accomplished by qualitatively and quantitatively comparing the lymphokine production of non-exposed and activated lymphocytes with the lymphokine production of exposed and acitivated lymphocytes in vitro. In another aspect of the invention, the method is utilized as a T cell tissue culture maintenance supplement to optimize their potential for T cell growth factor (TCGF) production, thereby maximizing the proliferation of the cultured T cells.

In yet another aspect of the invention, the method is utilized as a therapeutic approach for treating immune system depression resulting from elevated levels of GCS, either endogenously produced or exogenously administered, and as a therapy for reversing the age related decline in the biosynthesis of certain T cell lymphokines. In final aspects of the invention, the method is utilized as an adjuvant with vaccines to selectively direct the host immune responses toward protective, rather than pathologic or non-protective, pathways. This includes the possibility of employing the method to facilitate the desensitization to specific antigens in individuals with allergies.

DETAILED DESCRIPTION

The invention is a method for enhancing or maximizing the production of T-cell lymphokines, which comprises exposing T cell lymphocytes which have a potential to make selected T cell lymphokines to appropriate concentrations of particular steroid hormones prior to activation. The particular steroid hormone to which the T cell lymphocyte is exposed depends upon the lymphokine which is selected for enhancement or maximized production. The method works in vitro and in vivo in warm blooded animals which host the T cell lymphocytes. If the T cell lymphocytes are in a warm blooded animal, the exposure can be parenteral, transdermal or transmucosal.

As mentioned above, GCS have long been known as immunosuppressors. In accordance with the invention and contrary to the prior art, it has been found that pre-cellular activation exposure of T cell lymphocytes having a potential to make IL-4 to various types of natural and synthetic GCS at physiologic and pharmacologic concentrations results in the enhancement of IL-4 production. It has also been found that only at pharmacologic concentrations GCS depress the production of IL-2 and gamma interferon (g-IFN), while enhancing the production of IL-4. At physiologic concentrations, GCS enhance IL-4 production and have no effect on IL-2 and g-IFN production. Hydrocortisone, DEX and corticosterone are some of the GCS which work in accordance with this aspect of the invention.

Also in accordance with the invention, the steroid 1,25 $(OH)_2D_3$ enhances the production of IL-4 at physiologic and pharmacologic dose levels and, like GCS, inhibits IL-2 and g-IFN production at pharmacologic dose levels.

In further accordance with the invention, exposing T cell lymphocytes which have a potential to make selected T cell lymphokines to DHEA or a DHEA cogener prior to activation enhances the production of IL-2 and g-IFN. DHEA cogeners which are useful in the invention have the following structure:

in which R is hydrogen in alpha or beta configuration or nothing, resulting in a double bond between carbon atoms 5 and 6; $R_1$ is hydrogen or bromine or fluorine in alpha configuration; and $R_2$ is oxygen or methyl ketone ($—COCH_3$).

The selected steroid hormones may be administered to warm blooded animals through pre-cursor substances which are then metabolized to the steroid hormones. For instance, 25 hydroxy vitamin $D_3$ may be administered (preferably orally or by injection) and metabolized to 1,25 $(OH)_2D_3$. Also, the sulfanated form of DHEA (DHEA-S) may also be used in the method provided the T cell lymphocytes are in a warm blooded host and the DHEA-S is administered to the warm blooded host in a fashion (preferably orally or by injection) in which it may then be metabolized to DHEA by tissue-associated DHEA-sulfatases.

The simultaneous enhancement or maximization of the production of more than one T cell lymphokine may be achieved by exposing the T cell lymphocyte to more than one steroid hormone prior to activation. The exposure to more than one steroid hormone can be done simultaneously or sequentially. The concentration of each of the steroid hormones should be balanced to achieve the desired enhancing effects. For example, if it were desirous to enhance the production of IL-2, g-IFN and IL-4, the T cell lymphocytes could be exposed to physiologic or pharmacologic levels of DHEA and a physiologic level of GCS. This would avoid the IL-2 and g-IFN depression which is characteristic of a pharmacologic level of GCS.

Evidence derived from experimental and clinical observations indicates that immunologic reactions elicited to either simple or complex antigens often manifest as a balanced heterogeneous blend of both cellular and humoral components, with the fractional contribution of any individual type of effector mechanism oftentimes dominating the overall response. This level of heterogeneity, which is both quantitatively and qualitatively based, is essential to the development of a protective immune response (Parish, Transpl. Rev. 13:35 (1972); Katsura, Immunol. 32:227 (1977)). Alterations to this natural balance, whether caused by genetic or physiologic changes, can lead to a depressed capacity to elicit protective immune responses (Coutelier et al., J. J. Exp. Med. 165:64 (1987); Ogilvie et al., Cellular and Humoral Mechanisms in Anaphylaxis and Allergy, R. Karger, New York, p. 378 (1969); and Mayrhofer et al., Immunol. 37:145 (1979)), and might also lead to immunologic responses having pathologic consequences (Mayrhofer et al., Immunol. 37:145 (1979); Locksley et al., Ann. Inst. Past/Immunol. 138:744 (1987); and Tite et al., J. Immunol. 139:2892 (1987)).

Administration of steroid hormones in accordance with the invention would be useful in treating such immune system imbalances in warm blooded animals. Characteristic of this type of immunosuppression are abnormal levels of selected steroid hormones or abnormal ratios of selected steroid hormones. Immunosuppression in warm blooded animals may be mediated by endogenously or exogenously elevated GCS levels. Elevated GCS levels can result from a variety of causes including, but not limited to, viral infections, certain bacterial infections, certain parasitic infections, cancer, some autoimmune syndromes, stress, trauma, post-surgical trauma, burn trauma, as a secondary consequence to any clinical condition which causes an elevated production of IL-1, or therapeutic treatment for a variety of clinical conditions. The elevated GCS levels can result in an imbalance in the production of essential interleukins. The normal balance of essential interleukin production may be restored by administration of steroid hormones of the appropriate types and combination in accordance with the invention.

Additionally, if it were known that elevated GCS levels were the result of certain behavior or maladies, administration of antagonistic steroid hormones in accordance with the invention could be used as a prophylaxis prior to the onset of the elevation in GCS levels and resultant immunosuppression. For instance, there is a bovine malady commonly known as "Shipping Fever" wherein there is a high rate of morbidity and mortality associated with the stress induced by long distance bovine shipment. This stress is associated with chronic increased levels of GCS. Prophylactic administration of steroid hormones in accordance with the invention prior to bovine shipment would counteract the immunosuppressive effects of the chronically elevated GCS levels, and, therefore, reduce the risk of these animals to infectious agents.

The invention may also be used as a diagnostic tool in evaluating lymphokine production deficiency. In this application T cell lymphokine production of a first group of T cell lymphocytes which have a potential to make selected T cell lymphokines after T cell lymphocyte activation is measured. A second group of the same type of T cell lymphocytes is exposed to a particular steroid hormone prior to T cell lymphocyte activation. The selected T cell lymphkine production of the second group of T cell lymphocytes is then measured after activation. The amount of T cell lymphokine production of the two groups of T cell lymphokines are compared. The sensitivity of the diagnostic tool is maximized when the amount of the particular steroid hormone to which the second group of T cell lymphocytes is exposed is sufficient to maximize the production of the T cell lymphokines which the particular steroid hormone enhances. If the T cell lymphokine measured is IL-2 or g-IFN, the preferable steroid hormone may be selected from the group )HEA or a DHEA cogener having the structure recited above. If the T cell lymphokine measured is IL-4, the preferable steroid hormone may be selected from the group GCS or 1,25 $(OH)_2D_3$.

Another application of the invention is to use the method as a vaccine adjuvant to selectively direct the vaccine-induced immune response down a protective, rather than a potentially pathological or non-protective, immunologic pathway. Warm blooded animals, when immunized, will produce an immunologic response in which certain lymphokines are produced. When warm blooded animals are immunized with the same immunizing agent and a selected steroid hormone is administered in accordance with the invention prior to or contemporaneously with vaccination, certain lymphokine responses are greatly enhanced, directing the vaccine induced response down a protective immunologic pathway. Typical methods of administering the steroid hormone in this application of the invention include implants, mixing the steroid hormone with the immunizing agent, and topically applying the steroid hormone to skin sites above the site of vaccination. When it is desirous to promote cellular immunity, preferable vaccine adjuvants are steroid hormones selected from the group consisting of DHEA and DHEA cogeners having the structure recited above. When it is desirous to promote humoral immune responses, preferable vaccine adjuvents are steroid hormones selected from the group consisting of GCS or 1,25 $(OH)_2D_3$.

It is also believed that the invention can be used as a means to facilitate desensitization to agents to which a warm blooded animal is allergic. Desensitization of a warm blooded animal to an allergic agent is dependent upon induction by an allergic host of a secondary type of immunologic response not involving IgE. Since the administration of steroid hormones in accordance with the invention has proven to selectively promote immunologic responses that do not involve IgE, the method of the invention should work as an adjuvant to desensitization techniques.

Another application of the invention is to treat naturally occurring age-related decreases in immune function. Associated with age related decline in immune function is a decrease in the production of certain lymphokines. Treatment of aging, warm blooded animals with steroid hormones by the method of the invention substantially restores the production of selected lymphokines. For example, it has been found that treatment of aging mice with DHEA enhances the capacity of the animal's T cells to produce IL-2 and g-IFN to levels nearly equivalent to young control mice.

The invention and applications thereof are further described in connection with the following examples, which are intended to illustrate the invention, but not to limit the scope thereof.

EXAMPLE 1

Figure 1A:
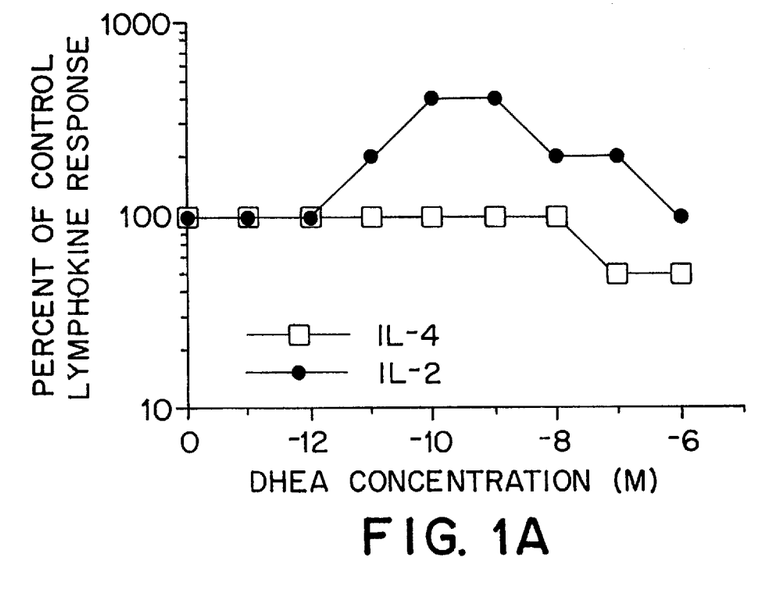
FIG. 1A is the dose response curve for DHEA of example 1.
Figure 1B:
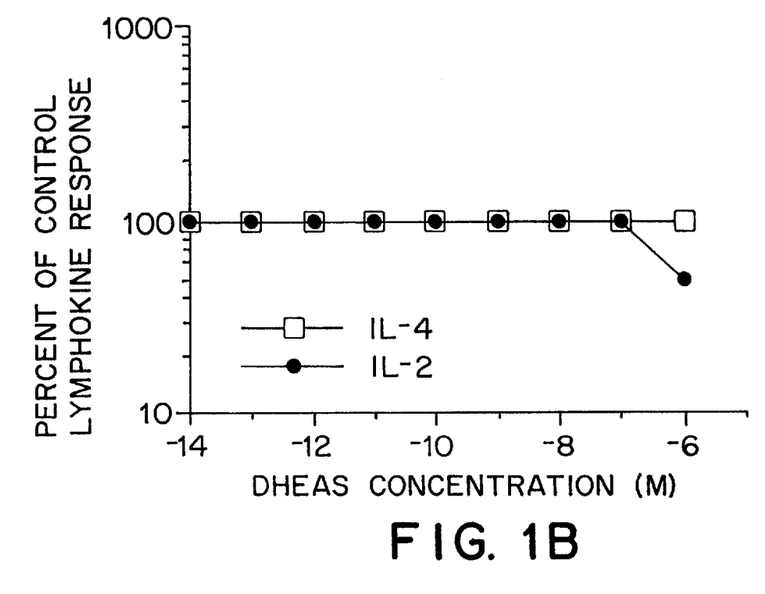
FIG. 1B is the dose response curve for DHEA-S of example 1.

DHEA enhances IL-2 Production by activated murine T cells. In this experiment the capacity of DHEA and DHEA-S to alter the production of IL-2 and IL-4 following in vitro lymphocyte treatment or exposure was evaluated. DHEA significantly enhanced the production of IL-2 over a wide dose range, and DHEA-S, over the same dose range, had no effect on IL-2 and IL-4 production. FIG. 1A is the dose response curve of DHEA and FIG. 1B is the dose reponse curve of DHEA-S developed in this experiment.

Spleen cells obtained from normal BALB/c mice were prepared as a single cell suspension at a concentration of $1 \times 10^7$ cells/ml in RPMI 1640 supplemented with 2 mM L-glutamine, $5 \times 10^{-5}$M 2-mercaptoethanol, 20 ug/ml gentamycin-sulfate, and 1% Nutridona-NS (Boehringer-Mannheim). Individual aliquots of cells were then pulsed for 30 minutes at 37° C. with the indicated concentrations of DHEA or DHEA-S. After pulsing, the cells were washed several times in balanced salt solution, resuspended in fresh medium, and then dispensed into 24-well culture plates with a stimulatory concentration of anti-CD3 (Leo et al. Proc. Natl. Acad. Sci. U.S.A., 84:1374 (1987)). After a 24-hour incubation period, culture supernatants were harvested for assessment of IL-2 and IL-4 activity using the method of Mossman (J. Immunol. Meth. 65:55 (1983)). In this experiment, 100% control titers of IL-2 and IL-4 from normal stimulated splenocytes in FIG. 1A were 640 and 160 units/ml, respectively. For control splenocytes from FIG. 1B, 100% control titers of IL-2 and IL-4 were 2560 and 320 units/ml, respectively.

This same experiment was repeated to assay for g-IFN production. A dose response curve similar to that reported in FIG. 1A for DHEA was obtained for g-IFN.

This same experiment was performed using the DHEA cogener 16 alpha bromo DHEA in place of DHEA. A dose response curve similar to that reported in FIG. 1A was obtained for 16 alpha bromo DHEA.

EXAMPLE 2

DHEA enhances IL-2 production in GCS-treated normal splenocytes and cloned T cell lines. In this series of experiments the capacity of DHEA to facilitiate a reversal of glucocorticoid-induced suppression of IL-2 production by either normal murine lymphocytes, or cloned T cell lines with similarities to either Th1-type or Th2-type helper T cells was evaluated.

Figure 2A:
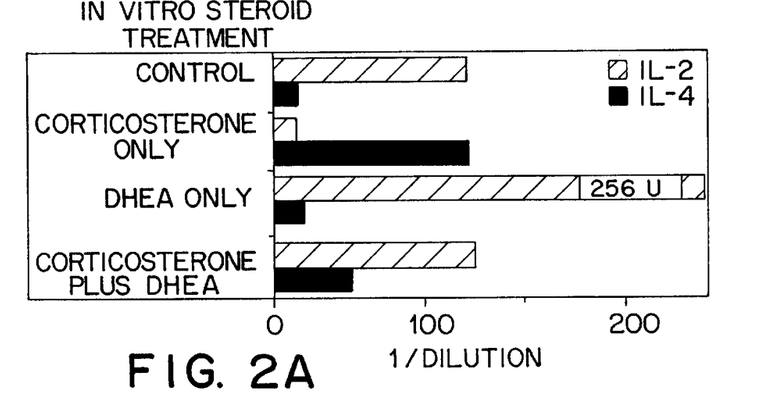
FIG. 2A presents the lymphokine response of DHEA and Corticosterone treated normal lymphocytes of example 2.

Referring to FIG. 2A exposure of splenocytes to the effects of Corticosterone ($10^{-7}$M) greatly reduced the capacity of cells to produce IL-2 subsequent to activation with anti-CD3. DHEA treatment alone augmented IL-2 production. Lymphocytes exposed to Corticosterone and DHEA, followed by their activation in vitro, produced normal or enhanced levels of IL-2 and enhanced levels of IL-4.

Figure 2B:
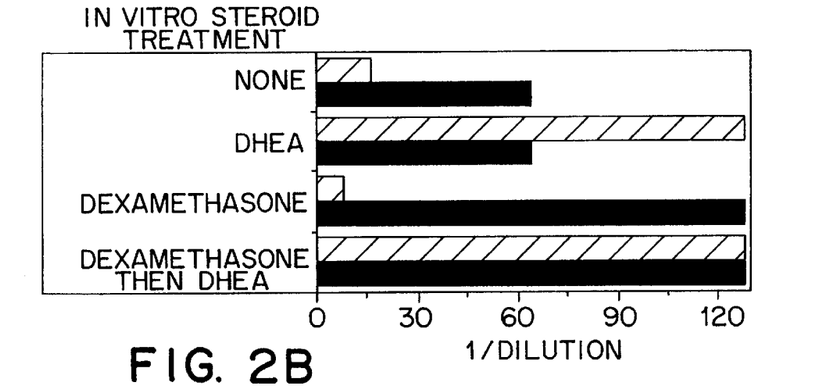
FIG. 2B presents the lymphokine response of DHEA and Dexamethasone (DEX) treated OVA/2 of example 2.
Figure 2C:
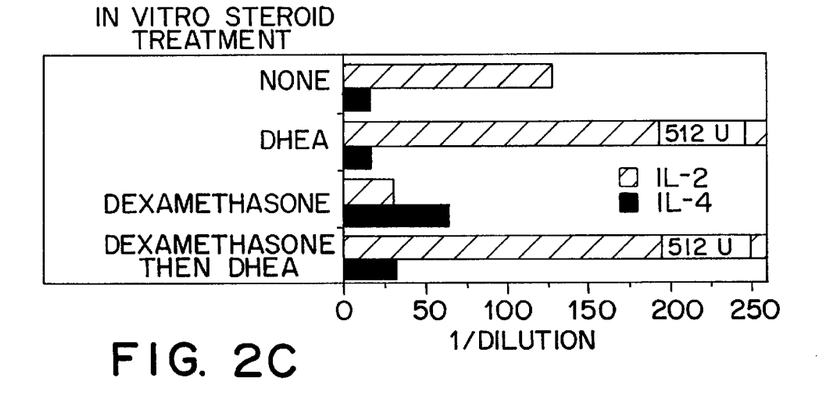
FIG. 2C presents the lymphokine response of DHEA and DEX treated OVA/3 of example 2.
Figure 3:
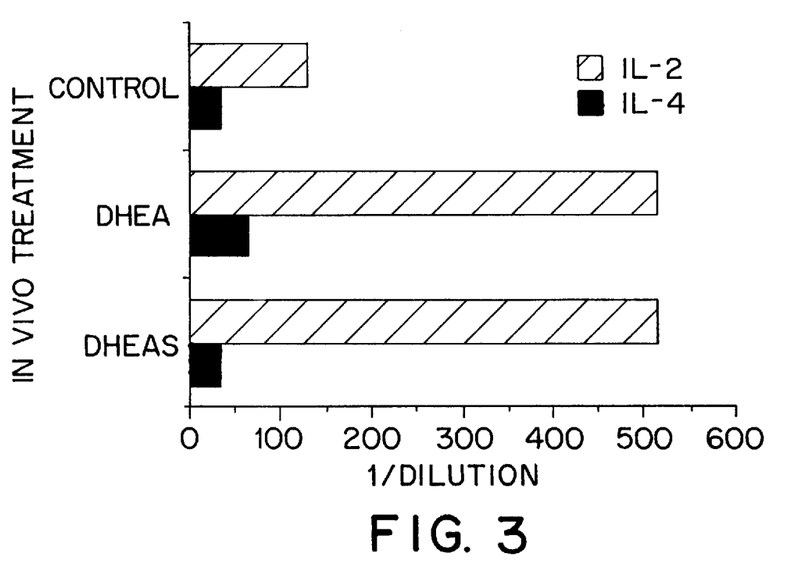
FIG. 3 presents the lymphokine response of DHEA or DHEA-S treated animals.

Referring to FIG. 2B and FIG. 2C, OVA/2 (an ovalbumin (OVA)-specific cloned T cell line with characteristics similar to Th2-type cells), and OVA/3 (a cloned T cell line with characteristics similar to Th1-type cells), were exposed in vitro to the effects of DHEA and/or glucocorticoids prior to their culture with antigen and syngeneic antigen-presenting cells. As shown in FIG. 2C, DHEA treatment of OVA/3 greatly augmented the capacity of this cell line to produce IL-2, while exposure to DEX resulted in an IL-4 dominant phenotype, similar to what is observed with Th2-type clones. Treatment of OVA/3 with DEX followed by DHEA, resulted in a marked elevation in IL-2 production with only a minimal enhancement of IL-4. As shown in FIG. 2B, the effects of steroid treatment on the capacity of OVA/2 to produce TCGF gave comparable results. DHEA exposure of this T cell clone was capable of shifting the pattern of TCGF production from a Th2-like to a Th1-like phenotype (IL-2 dominant), while DEX treatment alone augmented IL-4 production following activation in vitro with OVA. Treatment of OVA/2 with both DEX and DHEA caused an enhanced capacity to produce both IL-2 and IL-4.

Single cell suspensions of normal murine spleen cells were prepared in Nutridoma-supplemented complete RPMI at $10^7$ cells/ml. They were then pulsed with $10^{-7}$M Corticosterone and/or $10^{-8}$M DHEA as described in FIG. 2A. After several washes, the cells were stimulated with anti-CD3. The enhancement of IL-2 production by DHEA exposed normal splenocytes is reported in FIG. 2A. FIG. 2C and FIG. 2D describe the regulation of lymphokine production by two ovalbumin (OVA)-specific cloned T cell lines. The OVA-specific T cell clones were derived from nylon-wool enriched splenic T cells from OVA-immunized (C3H× C57/B6)$F_1$ mice using the method of Berzofsky (J. Immunol. 35:2628 (1985)). OVA/3 and OVA/2 cell lines were derived from different clonings, each having distinct patterns of lymphokine production. Culture conditions and assay procedures for IL-2 and IL-4 are as in Example 1.

EXAMPLE 3

A single injection of mice with DHEA or DHEAS enhanced the biosynthesis of IL-2 by activated lymphoid cells. In this experiment the effects of in vivo administration of DHEA and DHEA-S on IL-2 and IL-4 biosynthesis are demonstrated. Groups of (C3H×BL/6)$F_1$ mice were given a single intraperitoneal injection of 100 ug DHEA or DHEAS. After three days, spleen cells from the treated groups, plus spleen cells from an untreated age-matched control group, were prepared for culture as described in Example 1. The relative titers of IL-2 and IL-4 in the 24-hour culture supernatants were determined in the presence of anti-IL-2, or anti-IL-4, both anti-IL-2 and anti-IL-4, or no blocking antibodies. The assay was read visually. Non-activated cultured lymphoid cells produced undetectable (less than 2 Units) of either IL-2 or IL-4.

EXAMPLE 4A

Figure 4A:
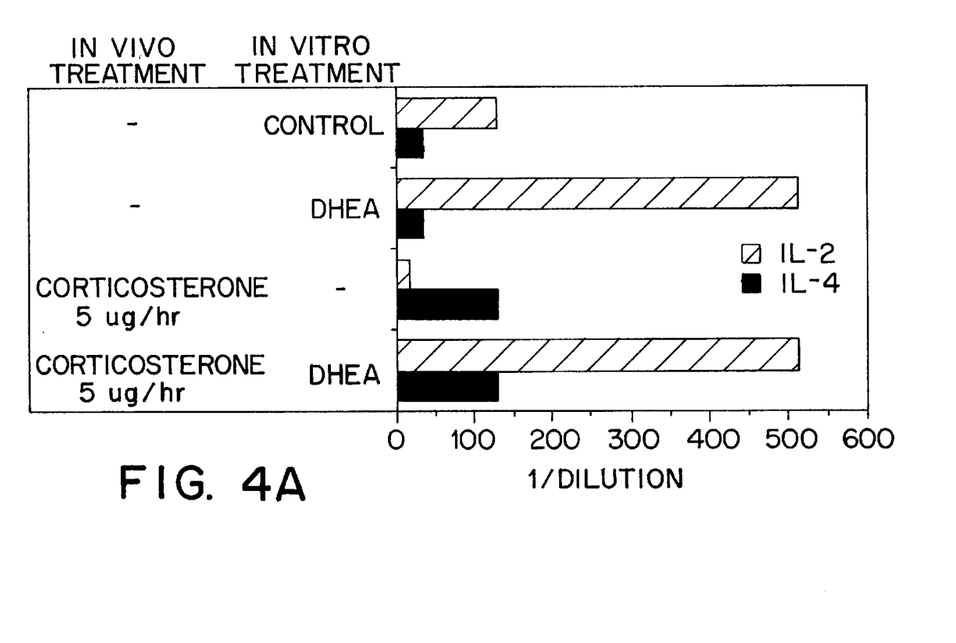
FIG. 4A presents the experimental results of example 4A.

DHEA enchances IL-2 Production in splenocytes from corticosterone-treated mice. This experiment demonstrates the reversal of the inhibitory effects caused by chronic glucocorticoid administration to normal mice in vivo on the capacity of their T cells to produce IL-2. A short pulse with DHEA ($10^{-8}$) in vitro prior to lymphocyte activation caused a significant enhancement of IL-2 production. Under these conditions, the glucocorticoid-induced augmentation in IL-4 synthesis was not affected, resulting in a population of lymphoid cells capable of producing high levels of both IL-2 and IL-4. Biodegradable pellets (Innovative Research, Inc.) containing corticosterone and designed to deliver this steroid at a dose of 5 ug/hr were implanted subcutaneously into (C3H×B46) $F_1$ mice 72 hours prior to the harvesting of the splenocytes for culture. Culture and assay procedures are as described in Example 1. The results are presented in FIG. 4A.

EXAMPLE 4B

DHEA in vivo enhances IL-2 production in mice with and without corticosterone treatment. This experiment demonstrates that DHEA administered in vivo influences the profile of TCGF produced by splenocytes isolated from these treated animals. The stimulation of splenocytes isolated from normal animals consistently gave a standard pattern of TCGF production where IL-2 dominated over IL-4. Lymphocytes isolated from corticosterone-treated animals (5 ug/hr) demonstrated a marked reversal of this pattern where IL-4 consistently represented the dominant TCGF. Similar to what is observed following an in vitro treatment with this androgen steroid, activated splenocytes from DHEA-treated animals (5 ug/hr) exhibited an enhancement in IL-2 production. Under conditions where both steroids were therapeutically elevated in vivo, it was found that isolated splenocytes from these animals produced enhanced levels of both IL-2 and IL-4 subsequent to their activation with anti-CD3 in vitro.

Figure 4B:
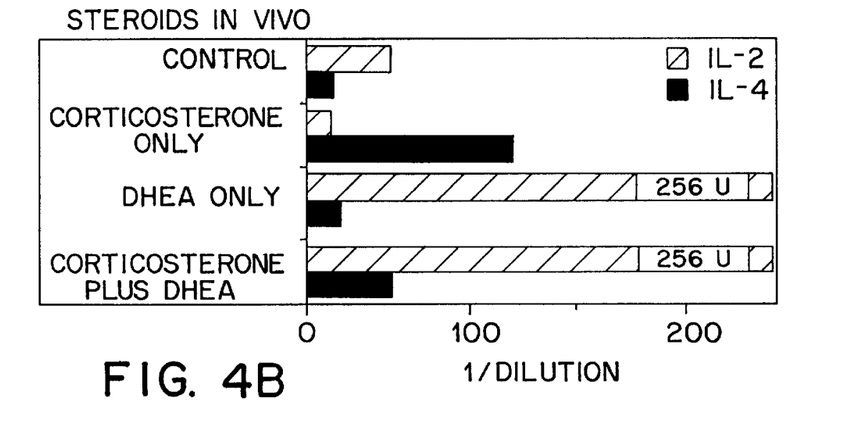
FIG. 4B presents the experimental results of example 4B.

Biodegradable pellets (Innovative Research, Inc.) containing corticosterone or DHEA that deliver their drugs 5 ug/hour were implanted subcutaneousely into three separate groups of BALB/c mice 72 hours prior to harvesting and preparation of spleen cells. Single cell preparations of splenocytes from each group were cultured as described in Example 1 and stimulated with the polyclonal T cell mitogens anti-CD3. After 24 hours, culture supernatants were collected and assayed for IL-2 and IL-4 activity as described in Example 1. The experimental results are reported in FIG. 4B.

EXAMPLE 5

Figure 5A:
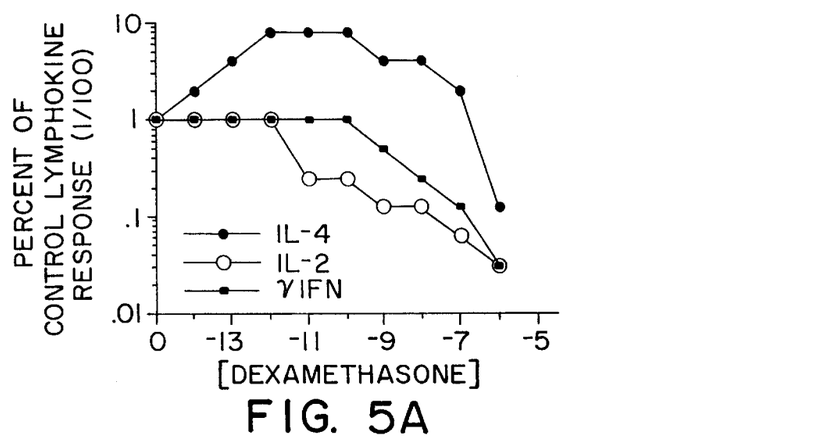
FIG. 5A is the dose response curve for DEX of example 5.
Figure 5B:
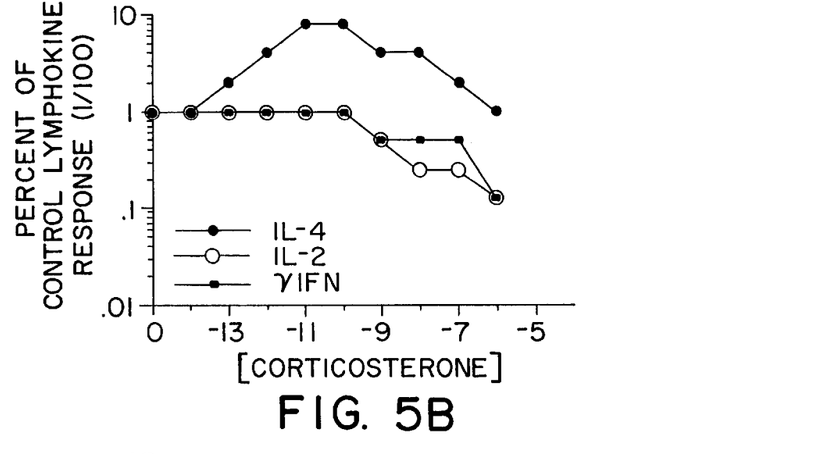
FIG. 5B is the dose response curve for Corticosterone of example 5.
Figure 5C:
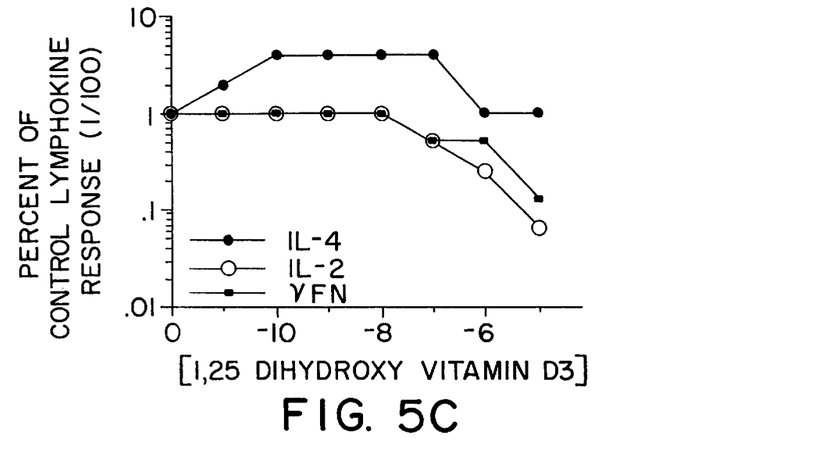
FIG. 5C is the dose response curve for 1,25 dihydroxy vitamin D3 ($1,25(OH)_2D_3$) of example 5.

Dose-dependent inhibition of IL-2 and g-IFN with a simultaneous activation of IL-4 by glucocorticoids and 1,25 dihydroxyvitamin D3. This experiment demonstrates that glucocorticosteroids and 1,25(OH)$_2$D$_3$, at physiological dose levels, enhance the production of IL-4 without affecting IL-2 and g-IFN production, and, at pharmacological dose levels, enhance the production of IL-4 and inhibit the production of IL-2 and g-IFN. (C3H×BL/6)$F_1$ mice were immunized by subcutaneous immunization in the flank region with 100 ug OVA/CFA. Two weeks later, single cell suspensions of spleens were prepared in Nutridoma-supplemented, complete RPMI at 1×10$^7$ cells/ml. Referring to FIG. 5A, a portion of the cells were subdivided into groups containing the indicated concentrations of DEX and incubated for 30 minutes at 37° C. Referring to FIG. 5B, cells were treated with corticosterone. Referring to FIG. 5C, cells were treated with 1,25(OH)$_2$D$_3$. After multiple washes, cells were dispensed into culture wells in 1 ml volumes at 1×10$^7$ cells/ml with either no antigen or 100 ug OVA. After a 24-hour incubation period in a humidified CO$_2$ incubator, the culture supernatants were harvested for assessment of IL-2 and IL-4 activity using a modification of the method of Mosmann (J. Immunol Meth., 65:55 (1983)). g-IFN was evaluated using a modification of the method of Green (Green et al. J. Clin. Microbiol., 12:433 (1980)). All groups cultured without antigen produced less than 1 Unit IL-2 or IL-4 and no detectable g-IFN.

EXAMPLE 6

In this series of experiments the use of the invention as a vaccine adjuvant is demonstrated.

Figure 6A:
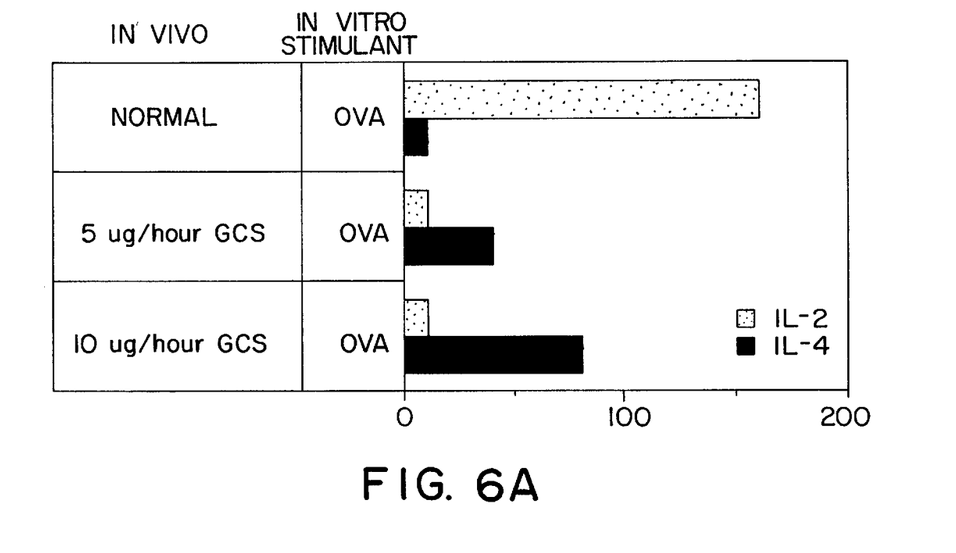
FIG. 6A presents the results of example 6 wherein GCS is used as a vaccine adjuvant.

T cells from corticosterone-treated mice Produce low titers of IL-2 and elevated titers of IL-4 in vitro. C3H mice received implants of biodegradable corticosterone pellets designed to deliver steroid at a rate of 5 or 10 ug/hour. The day after implantation, both the steroid treated groups and a normal control group of mice were immunized in the hind footpads with 100 ug OVA in CFA. Ten days after immunization, the draining lymph nodes and spleens from all groups were prepared for culture. Lymph node cells were stimulated with 100 ug OVA. Culture supernatants were assayed for IL-2 and IL-4 activity after 24 hours using the HT-2 bioassay. The experimental results are reported in FIG. 6A. Similar alterations in the ability of antigen-activated T cells to product IL-2 and IL-4 were observed when the steroid hormone was mixed with the immunizing antigen, or topically applied to skin sites above the site of vaccination.

Figure 6B:
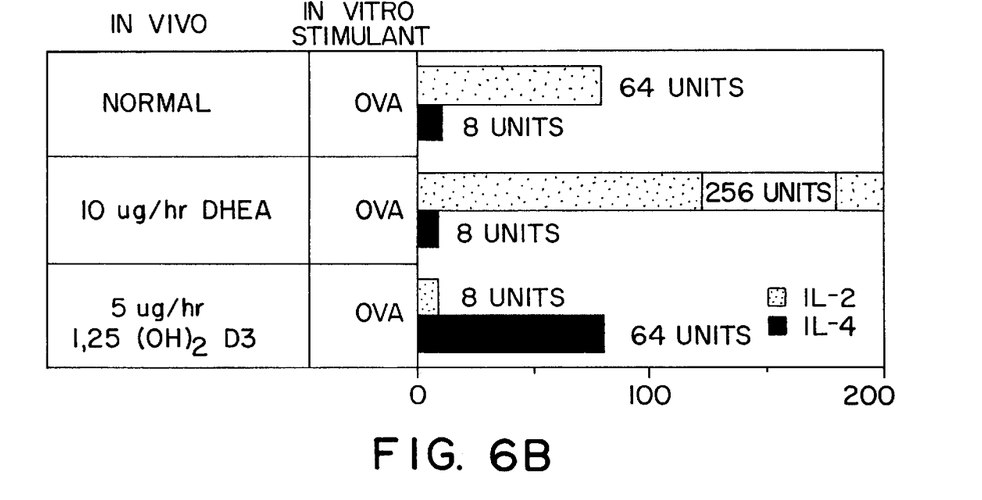
FIG. 6B presents the results of example 6 wherein DHEA and $1,25(OH)_2D_3$ are used as vaccine adjuvants.

T cells from 1,25-dihydroxyvitamin D3-treated mice produce low titers of IL-2 and elevated titers of IL-4 in vitro. T cells from DHEA-treated mice produce elevated titers of IL-2 in vitro. C3H mice received implants of biodegradable DHEA or 1,25(OH)$_2$D$_3$ pellets designed to deliver steroid at a rate of 5 and 10 ug/hour, respectively. Three days after implantation, both the steroid treated groups and a normal control group of mice were immunized in the hind footpads with 100 mg OVA in CFA. Ten days after immunication, the draining lymph nodes and spleens from all groups were prepared for culture. Lymph node cells were stimulated with 100 ug OVA. Culture supernatants were assayed for IL-2 and IL-4 activity after 24 hours using the HT-2 bioassay. The experimental results are reported in FIG. 6B. Similar alterations in the ability of antigen-activated T cells to produce IL-2 and IL-4 were observed when the steroid hormone was mixed with the immunizing antigen, or topically applied to skin sites above the site of vaccination.

EXAMPLE 7

This series of experiments demonstrates age related decline in certain lymphokine production in warm blooded animals and restoration of certain lymphokine production in old warm blooded animals by appropriate steroid hormone treatment in accordance with the invention. The particular lymphokines assayed are IL-2, IL-4 and g-IFN and the steroid hormone administered is DHEA.

Figure 7A:
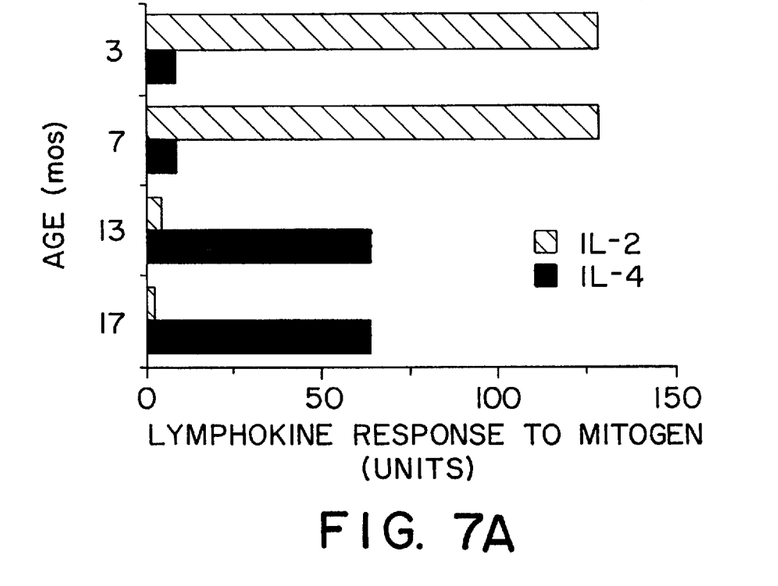
FIG. 7A presents the age-associated changes in lymphokine production in mice demonstrated in example 7.

Aging is associated with a reduction in the ability of activated T cells to product IL-2, and a parallel increase in the production of IL-4. Referring to FIG. 7A, (C3H×BL/6) $F_1$ mice of the indicated ages were sacrificed and their spleen cells prepared for culture with mitogen, anti-CD3. Culture supernatants were harvested and evaluated for the relative contribution of IL-2 and IL-4 using the HT-2 bioassay. Non-activated cells product less than 1 Unit of either IL-2 or IL-4.

Figure 7B:
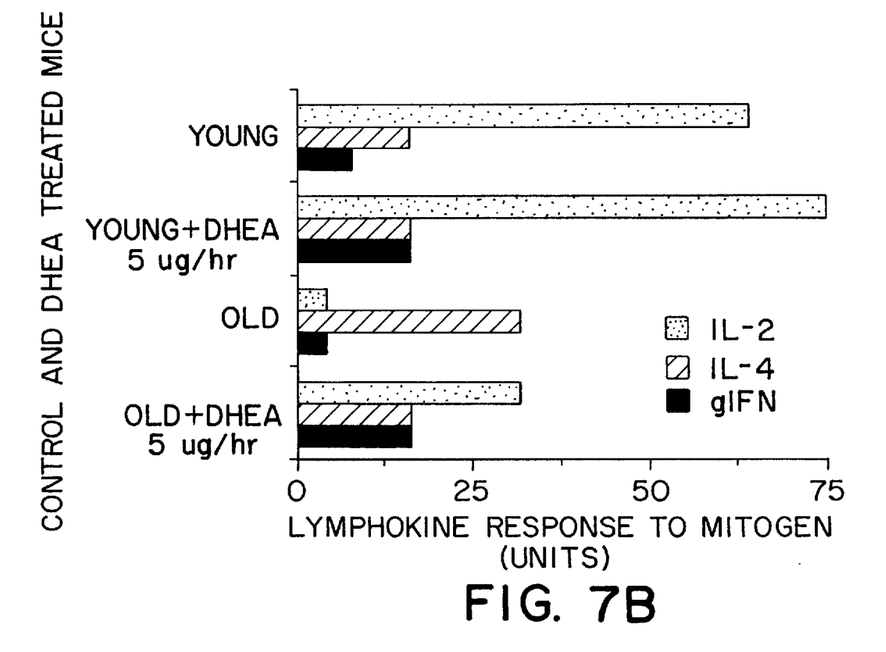
FIG. 7B presents the restoration of lymphokine production in old mice by DHEA demonstrated in example 7.

DHEA treatment of old mice enhances the capacity of their T cells to produce IL-2 and g-IFN following activation to levels nearly equivalent to young control mice. Referring to FIG. 7B, both young (6 mos.) and old (16 mos.) mice were implanted with DHEA pellets at a dose of 5 ug/hour. After three days, DHEA groups and control age-matched groups were sacrificed and their spleen cells prepared for culture with the mitogen anti-CD3. Culture supernatants were harvested and evaluated for the relative contribution of IL-2 and IL-4 using the HT-2 bioassay, and for g-IFN using the assay of Green. Non-activated cells produce less than 1 Unit of either IL-2 of IL-4 and no detectable g-IFN. Similar enhancement in the capacity of lymphocytes derived from old mice to produce IL-2 was observed following a direct exposure in vitro to DHEA ($10^{-9}$M–$10^{-7}$M).

Whereas this invention is here illustrated and described with specific reference to an embodiment thereof presently contemplated as the best mode in carrying out such invention, it is to be understood that various changes may be made in adapting the invention to different embodiments without departing from the broad inventive concepts disclosed herein and comprehended by the claims that follow:

We claim:

1. A method for enhancing the production of interleukin-2 and gamma interferon, which comprises exposing, prior to cellular activation by an antigen said cellular activation being production of interleukin-2 and gamma interferon as a result of exposure to an antigen, T cell lymphocytes having a potential to make interleukin-2 and gamma-interferon to dehydroepiandrosterone-sulfate (DHEA-S) in an amount effective for enhancing the production of interleukin-2 and gamma interferon, to produce exposed T cell lymphocytes, and cellularly activating by an antigen said exposed T cell lymphocytes to produce enhanced levels of interleukin-2 and gamma-interferon.

2. The method of claim 1 wherein said exposure is by oral administration of DHEA-S.

3. The method of claim 1 wherein said T cell lymphocytes are in a warm-blooded animal.

4. The method of claim 2 wherein said T cell lymphocytes are in a warm-blooded animal.

5. The method of claim 3 wherein said warm-blooded animal is a human.

6. The method of claim 4 wherein said warm-blooded animal is a human.

* * * * *